US00PP30643P2

(12) United States Plant Patent
Trees

(10) Patent No.: US PP30,643 P2
(45) Date of Patent: Jul. 2, 2019

(54) ***VERBENA* PLANT NAMED 'BALENDINZ'**

(50) Latin Name: ***Verbena* hybrid**
Varietal Denomination: Balendinz

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/932,136

(22) Filed: Feb. 7, 2018

(51) Int. Cl.
*A01H 5/02* (2018.01)

(52) U.S. Cl.
USPC ..... Plt./308
CPC ..... *A01H 5/02* (2013.01)

(58) Field of Classification Search
USPC ..... Plt./308
See application file for complete search history.

*Primary Examiner* — Anne Marie Grunberg
(74) *Attorney, Agent, or Firm* — Audrey Charles

(57) ABSTRACT

A new and distinct cultivar of *Verbena* plant named 'Balendinz', characterized by its medium rose, light pink, and white-colored flowers, dark green-colored foliage, and vigorous, mounded-spreading growth habit, is disclosed.

1 Drawing Sheet

Latin name of genus and species of plant claimed: *Verbena* hybrid.
Variety denomination: 'Balendinz'.

BACKGROUND OF THE INVENTION

The present invention relates to a new and distinct cultivar of *Verbena* plant botanically known as *Verbena* hybrid and hereinafter referred to by the cultivar name 'Balendinz'.

The new cultivar originated in a controlled breeding program in Guadalupe, Calif. during June 2013. The objective of the breeding program was the development of *Verbena* cultivars that are durable to environmental stresses, have dark green-colored foliage, and a mounded-spreading growth habit.

The new *Verbena* cultivar is the result of cross-pollination. The female (seed) parent of the new cultivar is the proprietary *Verbena* hybrid breeding selection coded 13760 (1958-1), not patented, characterized by its dark pink-colored flowers, dark green-colored foliage, and moderately vigorous, spreading growth habit. The male (pollen) parent of the new cultivar is LANAI Twister Pink 'Flagdena', U.S. Plant Pat. No. 22,438, characterized by its tri-colored, white and two-toned red-purple colored flowers, medium green-colored foliage, and moderately vigorous, trailing growth habit. The new cultivar was discovered and selected as a single flowering plant within the progeny of the above stated cross-pollination during August 2014 in a controlled environment in Guadalupe, Calif.

Asexual reproduction of the new cultivar by terminal stem cuttings since August 2014 in Guadalupe, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balendinz' as a new and distinct cultivar of *Verbena* plant:

1. Medium rose, light pink, and white-colored flowers;
2. Dark green-colored foliage; and
3. Vigorous, mounded-spreading growth habit.

Plants of the new cultivar differ from plants of the female and male parents primarily in having a different flower color, more growth vigor, and a more mounded growth habit.

Of the many commercially available *Verbena* cultivars, the most similar in comparison to the new cultivar is EnduraScape Pink Bicolor 'Balendpibi', U.S. Plant Pat. No. 28,455. However, in side by side comparisons, plants of the new cultivar differ from plants of 'Balendpibi' in at least the following characteristics:

1. Plants of the new cultivar have a flower color that is different from plants of 'Balendpibi';
2. Plants of the new cultivar have smaller leaves than plants of 'Balendpibi'; and
3. Plants of the new cultivar are shorter than plants of 'Balendpibi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balendinz'. The plants were grown in 4-inch pots for 12 weeks in a greenhouse in West Chicago, Ill. Plants were given one pinch one week after transplant.

DETAILED BOTANICAL DESCRIPTION

Figure 1:
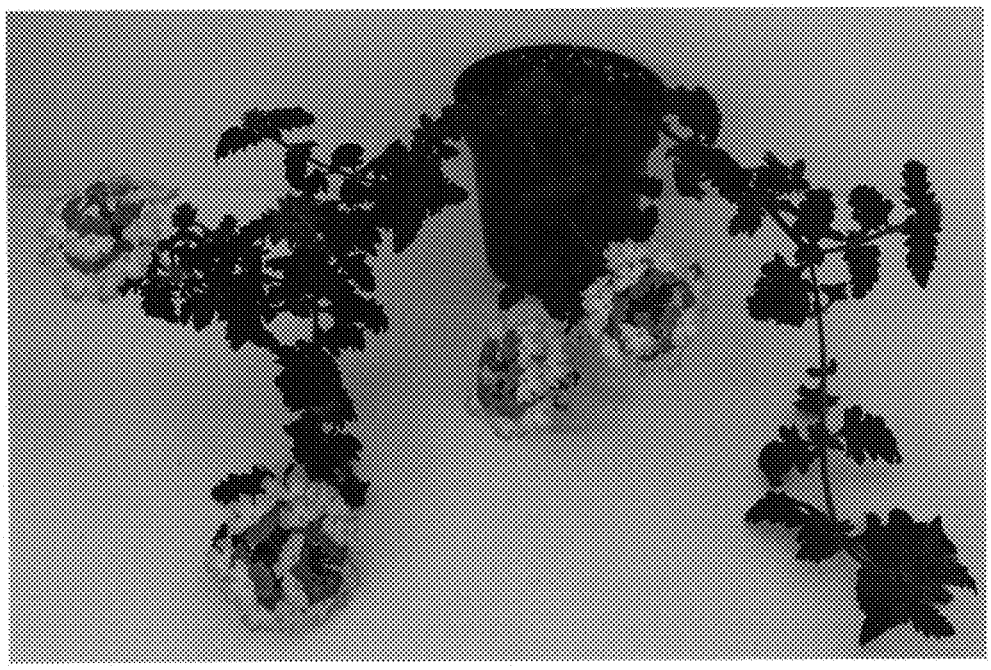
FIG. 1 illustrates a side view of the overall growth and flowering habit of 'Balendinz'.
Figure 2:
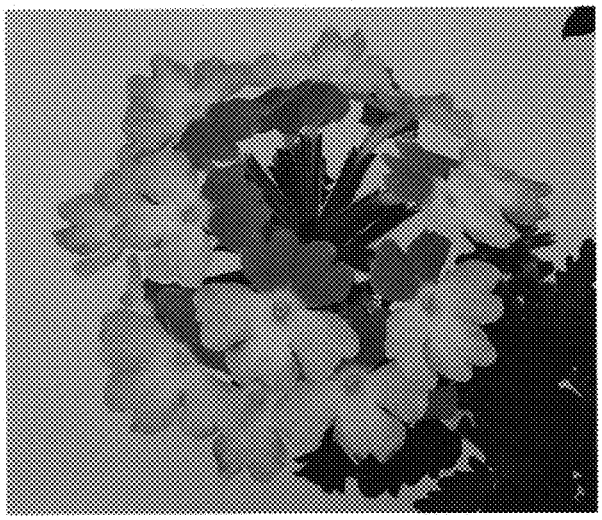
FIG. 2 illustrates a close-up view of an individual inflorescence of 'Balendinz'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2018 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 12 weeks utilizing a soilless growth medium. Plants were given one pinch one week after transplant. Greenhouse temperatures were maintained at approximately 68° F. to 72° F. (20° C. to 22° C.) during the day and approximately 64° F. to 66° F. (18° C. to 19° C.) during the night. Supplemental lighting was used. Measurements and numerical values represent averages of typical plants.

Botanical classification: *Verbena* hybrid 'Balendinz'.

Parentage:

*Female parent*.—Proprietary *Verbena* hybrid breeding selection coded 13760(1958-1), not patented.

*Male parent*.—LANAI Twister Pink 'Flagdena', U.S. Plant Pat. No. 22,438.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Vigorous, mounded-spreading.

*Size*.—Height from soil level to top of plant plane: Approximately 8.0 cm. Width: Approximately 44.0 cm.

*Branching habit*.—Freely branching, pinching enhances basal branching. Quantity of main branches per plant: Approximately 4.

*Branch*.—Shape: Square in cross section. Strength: Strong. Length: Approximately 25.0 cm. Diameter: Approximately 3.0 mm. Length of central internode: Approximately 3.0 cm. Texture: Densely pubescent with a mixture of glandular and nonglandular hairs. Gland color: Mixture of N92C and colorless, transparent. Color of young stems: 144A. Color of mature stems: 137B.

Foliage description:

*General description*.—Quantity of leaves per main branch: Approximately 16. Fragrance: None detected. Form: Simple. Arrangement: Opposite.

*Leaves*.—Aspect: Perpendicular to stem, obtuse angle with age. Shape: Ovate to oblong. Margin: Crenate. Apex: Broadly acute. Base: Truncate. Venation pattern: Pinnate. Length of mature leaf: Approximately 3.5 cm. Width of mature leaf: Approximately 2.8 cm. Texture of upper surface: Moderately pubescent. Texture of lower surface: Densely pubescent with a mixture of glandular and nonglandular hairs. Gland color: Colorless, transparent. Color of upper surface of young and mature foliage: Closest to but darker than NN137A with venation of 147C. Color of lower surface of young and mature foliage: Closest to NN137D with venation of 147C.

*Petiole*.—Length: Approximately 5.0 mm. Diameter: Approximately 2.0 mm. Texture: Densely pubescent with a mixture of glandular and nonglandular hairs. Gland color: Mixture of N92C and colorless, transparent. Color: 147C.

Flowering description:

*Flowering habit*.—'Balendinz' is freely flowering under outdoor growing conditions with substantially continuous blooming from spring through autumn and year-round in greenhouse environment.

*Lastingness of individual flower on the plant*.—Approximately 5 to 7 days.

Inflorescence description:

*General description*.—Type: Corymb. Shape: Hemispherical. Quantity per plant: Approximately 4. Fragrance: None detected. Length or height: 3.0 cm. Width: Approximately 6.0 cm. Quantity of fully open flowers per inflorescence: Approximately 16.

*Peduncle*.—Strength: Strong. Aspect: Erect. Length: Approximately 5.5 cm. Diameter: Approximately 2.0 mm. Texture: Densely pubescent with a mixture of glandular and nonglandular hairs. Gland color: Mixture of N92C and colorless, transparent. Color: 137B.

Flower description:

*General description*.—Type: Sessile, salverform.

*Bud*.—Rate of opening: Generally takes 2 to 3 days for bud to progress from first color to fully open flower. Quantity of unopened inflorescences per plant: Approximately 3.

*Bud just before opening*.—Shape: Elongated, globular at apex. Length: Approximately 1.3 cm. Diameter: Approximately 3.0 mm. Color: Petal portion 70C, sepal portion 137B.

*Corolla*.—Shape: Round. Diameter: Approximately 1.9 cm. Depth: Approximately 2.6 cm.

*Petals*.—Quantity: 5, fused at base forming a tube. Shape: Obovate. Appearance: Dull. Margin: Entire. Apex: Emarginate. Length of upper petals from tube: Approximately 8.0 mm. Width of upper petals: Approximately 6.0 mm. Length of lateral petals from tube: Approximately 9.0 mm. Width of lateral petals: Approximately 7.0 mm. Length of lower petal from tube: Approximately 9.0 cm. Width of lower petal: Approximately 8.0 mm. Texture of upper surface: Glabrous with glandular pubescent base. Texture of lower surface: Sparsely pubescent with a mixture of glandular and nonglandular hairs. Gland color: Mixture of N92C and colorless, transparent. Color of upper surface when first open: Lateral and lower petals NN155D with an overlay of 63C to 63B primarily on the outer edges; overlay can be heavier under higher light conditions; upper petals of 63B to 63A with NN155D at throat opening. Color of lower surface when first and fully open: NN155D with a faint overlay of 63D; overlay slightly heavier on upper petals. Color of upper surface when fully open: Lateral and lower petals NN155D with an overlay of 63C to 63B primarily on the outer edges; upper petals of 63B to 63A with NN155D at throat opening. Color of whiskers surrounding the opening of the corolla tube: NN155D.

*Corolla tube*.—Length: Approximately 2.0 cm. Diameter at proximal end: Approximately 1.0 mm. Diameter at distal end: Approximately 2.0 mm. Texture of outer surface: Upper half moderately glandular pubescent, lower half glabrous. Gland color: Colorless. Texture of inner surface: Densely pubescent. Color of outer surface: 145D with 145C at distal end. Color of inner surface: 145D with 145B at throat opening.

*Calyx*.—Shape: Tubular with 5 acute tips. Length: Approximately 1.2 cm. Width: Approximately 3.0 mm.

*Sepals*.—Quantity per flower: 5, fused at base. Shape: Linear. Apex: Acute. Length: Approximately 1.2 cm. Width: Approximately 1.0 mm. Texture of inner surface: Moderately pubescent. Texture of outer surface: Densely pubescent with a mixture of glandular and nonglandular hairs. Gland color: Mixture of N92C and colorless, transparent. Color of inner and outer surfaces: 137B.

*Stipules*.—Shape: Lanceolate. Apex: Acute. Length: Approximately 5.0 mm. Width at base: Approximately 1.0 mm. Texture of inner surface: Glabrous. Texture of outer surface: Densely pubescent with a mixture of glandular and nonglandular hairs. Gland color: Mixture of N92C and colorless, transparent. Color of inner and outer surfaces: 144A at base transitioning to 137A at apex.

*Reproductive organs*.—Androecium: Stamen quantity: 4, didynamous. Stamen length of longer pair: Approximately 2.0 mm. Stamen length of shorter pair: Approximately 1.0 mm. Anther shape: Bilobed, ovoid. Anther length: Approximately 1.0 mm. Anther color: N144D. Pollen amount: Moderate. Pollen color: 1D. Gynoecium: Pistil quantity: 1 per flower. Pistil length: Approximately 1.7 cm. Stigma shape: Bifid. Stigma length: Less than 1.0 mm. Stigma color: 137A. Style length: Approximately 1.6 cm. Style color: 145D with 145B near stigma. Ovary diameter: Approximately 1.0 mm. Ovary texture: Glabrous. Ovary color: 144A.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balendinz', substantially as herein illustrated and described.

* * * * *